United States Patent
Leobandung

(10) Patent No.: US 10,030,265 B2
(45) Date of Patent: Jul. 24, 2018

(54) DNA SEQUENCING USING MOSFET TRANSISTORS

(71) Applicant: International Business Machines Corporation, Armonk, NY (US)

(72) Inventor: Effendi Leobandung, Stormville, NY (US)

(73) Assignee: International Business Machines Corporation, Armonk, NY (US)

( * ) Notice: Subject to any disclaimer, the term of this patent is extended or adjusted under 35 U.S.C. 154(b) by 138 days.

(21) Appl. No.: 14/596,284

(22) Filed: Jan. 14, 2015

(65) Prior Publication Data
US 2016/0203258 A1    Jul. 14, 2016

(51) Int. Cl.
| | |
|---|---|
| C12Q 1/68 | (2018.01) |
| B01L 3/00 | (2006.01) |
| G01N 27/414 | (2006.01) |
| G01N 33/487 | (2006.01) |
| C12Q 1/6869 | (2018.01) |
| H01L 21/266 | (2006.01) |
| H01L 21/311 | (2006.01) |
| G01N 27/447 | (2006.01) |
| H01L 21/762 | (2006.01) |
| H01L 29/786 | (2006.01) |

(52) U.S. Cl.
CPC ...... *C12Q 1/6869* (2013.01); *B01L 3/502707* (2013.01); *B01L 3/502715* (2013.01); *B01L 3/502761* (2013.01); *G01N 27/4145* (2013.01); *G01N 27/4146* (2013.01); *G01N 27/4148* (2013.01); *G01N 33/48721* (2013.01); *H01L 21/266* (2013.01); *H01L 21/31111* (2013.01); *B81B 2201/058* (2013.01); *B81B 2201/06* (2013.01); *C12Q 2565/629* (2013.01); *G01N 27/44791* (2013.01); *H01L 21/762* (2013.01); *H01L 29/78696* (2013.01)

(58) Field of Classification Search
None
See application file for complete search history.

(56) References Cited

U.S. PATENT DOCUMENTS

| | | | |
|---|---|---|---|
| 7,863,140 B2 * | 1/2011 | Lim | G01N 27/4145 257/E21.051 |
| 8,444,835 B2 | 5/2013 | Elibol et al. | |

(Continued)

OTHER PUBLICATIONS

Appendix P: List of IBM Patents or Patent Applications Treated as Related, dated Oct. 31, 2016, pp. 1-2.

(Continued)

*Primary Examiner* — Mary Wilczewski
*Assistant Examiner* — Erik T Peterson
(74) *Attorney, Agent, or Firm* — Edward J. Wixted, III

(57) ABSTRACT

Embodiments of the invention include a method for fabricating a semiconductor device, the resulting structure, and a method for using the resulting structure. A substrate is provided. A hard mask layer is patterned over at least a portion of the substrate. Regions of the substrate not protected by the hard mask are doped to form a source region and a drain region. The hard mask layer is removed. A dielectric layer is deposited on the substrate. An insulative layer is deposited on the dielectric layer. A nano-channel is created by etching a portion of the insulative layer which passes over the source region and the drain region.

9 Claims, 6 Drawing Sheets

(56) References Cited

U.S. PATENT DOCUMENTS

| | | | |
|---|---|---|---|
| 8,470,408 B2 | 6/2013 | Branton et al. | |
| 8,563,240 B2 | 10/2013 | Su et al. | |
| 8,852,407 B2* | 10/2014 | Peng | G01N 33/48721 204/229.8 |
| 2003/0211502 A1* | 11/2003 | Sauer | C12Q 1/6869 435/6.11 |
| 2004/0238379 A1* | 12/2004 | Lindsay | C12Q 1/6825 205/792 |
| 2006/0246497 A1* | 11/2006 | Huang | G01N 27/4146 435/6.14 |
| 2007/0020416 A1* | 1/2007 | Dean | B29C 49/0005 428/35.7 |
| 2007/0178477 A1 | 8/2007 | Joiner, Jr. et al. | |
| 2008/0286767 A1* | 11/2008 | Miyahara | B01L 7/00 435/29 |
| 2010/0066348 A1* | 3/2010 | Merz | C12Q 1/6869 324/71.1 |
| 2010/0096268 A1* | 4/2010 | Ling | B82Y 15/00 204/549 |
| 2010/0243449 A1* | 9/2010 | Oliver | B82Y 30/00 204/450 |
| 2010/0310421 A1* | 12/2010 | Oliver | G01N 33/48721 422/82.01 |
| 2010/0327255 A1* | 12/2010 | Peng | B82Y 10/00 257/9 |
| 2011/0159481 A1 | 6/2011 | Liu et al. | |
| 2011/0204872 A1* | 8/2011 | Gridelet | G01N 27/4145 324/71.1 |
| 2011/0279125 A1* | 11/2011 | Bedell | B82Y 15/00 324/444 |
| 2012/0021918 A1* | 1/2012 | Bashir | B82Y 15/00 506/2 |
| 2012/0193237 A1* | 8/2012 | Afzali-Ardakani | B82Y 15/00 204/627 |
| 2014/0151228 A1* | 6/2014 | Royyuru | B82Y 15/00 204/451 |
| 2014/0248183 A1* | 9/2014 | Oliver | G01N 33/48721 422/82.01 |
| 2015/0028846 A1* | 1/2015 | Zhu | B82Y 15/00 324/71.5 |
| 2015/0268189 A1* | 9/2015 | Rigante | H01L 29/66795 257/253 |
| 2015/0316529 A1* | 11/2015 | Choi | G01N 33/48721 204/452 |
| 2016/0187282 A1* | 6/2016 | Gardner | C12Q 1/68 204/403.15 |

OTHER PUBLICATIONS

U.S. Appl. No. 15/338,734, filed Oct. 31, 2016; Entitled "DNA Sequencing using MOFET Transistors".

Esfandyarpour, et al.; "Microneedle Biosensor: A Method for Direct Label-free Real Time Protein Detection"; National Institutes of Health; Author Manuscript; Feb. 2013; 177:848-855. Copyright 2012.

Guo, et al.; "Computational Investigation of DNA Detection Using Single-Electron Transistor-Based Nanopore"; The Journal of Physical Chemistry; ACS Publicators; Copyright 2012; Published Sep. 19, 2012.

Huang, et al.; "Immobilized DNA Switches as Electronic Sensors for Picomolar Detection of Plasma Proteins"; JACS Articles; American Chemical Society; Copyright 2008, Published on Web Jun. 3, 2008.

Mali, et al.; "The dnaSET: A Novel Device for Single-Molecule DNA Sequencing"; IEEE Transactions on Electron Devices; vol. 51; No. 12; Dec. 2004.

Martinez, et al.; "Carbon nanotubes field effect transistors biosensors"; Mar. 2012.

* cited by examiner

DNA SEQUENCING USING MOSFET TRANSISTORS

BACKGROUND OF THE INVENTION

The present invention relates generally to the field of transistors, and more particularly to the use of metal-oxide-semiconductor field-effect transistor (MOSFET) transistors for sequencing deoxyribonucleic acid (DNA).

Since the onset of the human genome project in 1990, many different methods of sequencing DNA have been developed in the interest of reducing cost, required time, and sample volume while increasing accuracy. Common DNA sequencing technologies in use today include sequencing by synthesis (SBS) methods where the DNA nucleotide sequence is determined by the cyclic addition of nucleotide bases one base type at a time using either natural nucleotides or fluorescently-labeled nucleotides with a reversible terminator. Using these sequencing methods, sequence read length is very limited and accuracy is typically low. Traditionally, strategies such as parallelization and miniaturization are utilized to improve the reliability and read speed of SBS sequencing methods while reducing the associated cost.

The use of DNA sequencing technology for quickly, reliably, and inexpensively sequencing the genome of mammals such as human beings requires further advancements in the field and the development of new sequencing methodologies.

SUMMARY

Embodiments of the invention disclose a method of fabricating a semiconductor device, a sensor, and a method of sequencing DNA. A substrate is provided. A hard mask layer is patterned over at least a portion of the substrate. Regions of the substrate not protected by the hard mask are doped to form a source region and a drain region. The hard mask layer is removed. A dielectric layer is deposited on the substrate. An insulative layer is deposited on the dielectric layer. A nano-channel is created by etching a portion of the insulative layer which passes over the source region and the drain region.

DETAILED DESCRIPTION

Figure 1A:
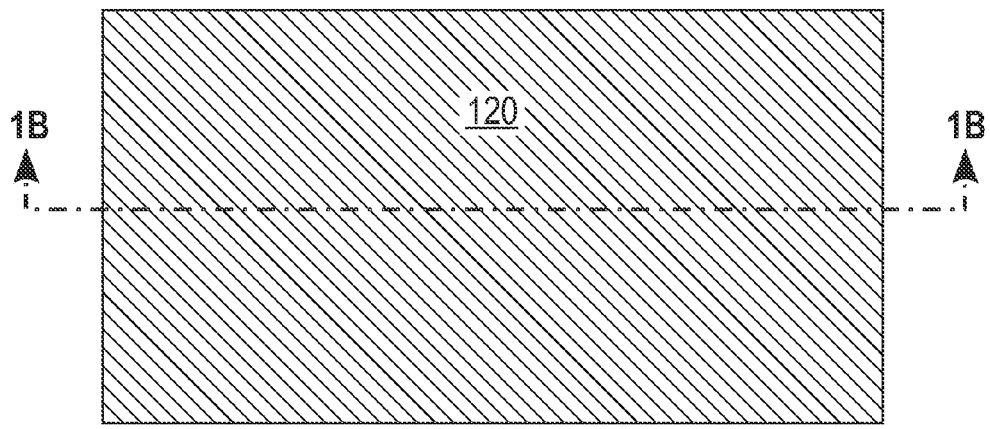
FIG. 1A depicts a top view of a semiconductor substrate and buried oxide layer on which a MOSFET device for sequencing DNA may be fabricated, in accordance with an embodiment of the invention.

Embodiments of the present invention generally provide a metal-oxide-semiconductor field-effect transistor (MOSFET) device for sequencing deoxyribonucleic acid (DNA). A detailed description of embodiments of the claimed structures and methods are included herein; however, it is to be understood that the disclosed embodiments are merely illustrative of the claimed structures and methods that may be embodied in various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper", "lower", "right", "left", "vertical", "horizontal", "top", "bottom", and derivatives thereof shall relate to the disclosed structures and methods, as oriented in the drawing figures. The terms "overlying", "atop", "positioned on" or "positioned atop" mean that a first element, such as a first structure, is present on a second element, such as a second structure, wherein intervening elements, such as an interface structure may be present between the first element and the second element. The term "direct contact" means that a first element, such a first structure, and a second element, such as a second structure, are connected without any intermediary conducting, insulating or semiconductor layers at the interface of the two elements.

Figure 1B:
FIG. 1B depicts a section view of a semiconductor substrate and buried oxide layer on which a MOSFET device for sequencing DNA may be fabricated, in accordance with an embodiment of the invention.

The present invention will now be described in detail with reference to the Figures. FIGS. 1A and 1B illustrate a top view and a section view of a starting wafer including buried oxide layer 110 and semiconductor substrate 120, in accordance with one embodiment of the invention. Semiconductor substrate 120 is a substrate on which a MOSFET device for sequencing DNA may be formed. Semiconductor substrate 120 is a semiconductor material, preferably a silicon-containing material including, but not limited to, silicon, germanium, silicon germanium alloys, germanium alloys, indium alloys, carbon nanotube, graphene, silicon carbon alloys, or silicon germanium carbon alloys. Semiconductor substrate 120 is present above buried oxide layer 110. Buried oxide layer 110 acts as an electrical insulator below semiconductor substrate 120. In general, the thickness of semiconductor substrate 120 is between 1 nm and 10 nm however, in embodiments of the invention where bulk silicon construction is used semiconductor substrate 120 may be thicker than 10 nm. While the depicted embodiment includes an illustration of silicon on insulator (SOI) construction, it should be appreciated by one skilled in the art that the invention is not limited to SOI construction, and that other types of semiconductor construction can be used in various embodiments of the invention, for example, bulk silicon construction. In embodiments where bulk silicon construction is used, buried oxide layer 110 may not be present in the starting wafer.

Figure 2A:
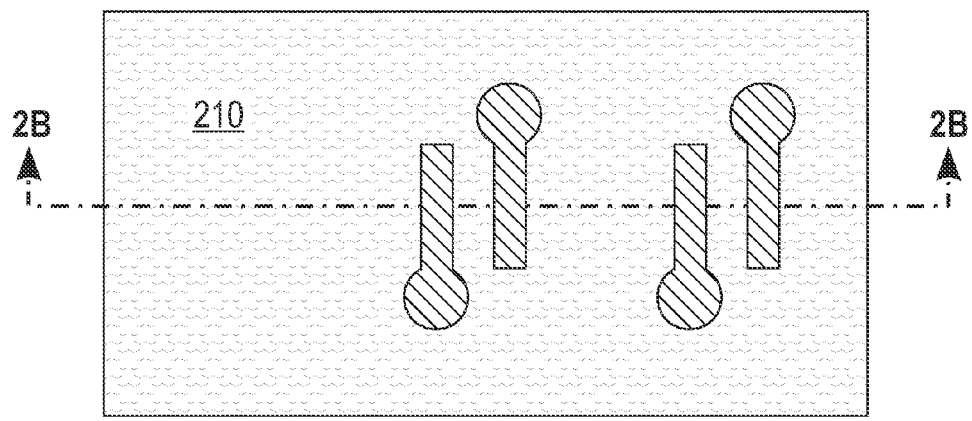
FIG. 2A depicts a top view of deposition and etching of a hard mask layer deposited on the semiconductor substrate of FIG. 1A, in accordance with an embodiment of the invention.
Figure 2B:
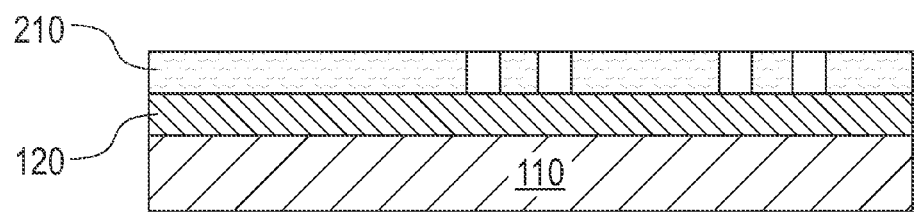
FIG. 2B depicts a section view of deposition and etching of a hard mask layer deposited on the semiconductor substrate of FIG. 1A, in accordance with an embodiment of the invention.

FIGS. 2A and 2B illustrate a top and section view of deposition and patterning of hard mask layer 210. Hard mask layer 210 is used to define an area of semiconductor substrate 120 which is to be doped during formation of source and drain terminals, as described in reference to the following Figures. In a preferred embodiment, hard mask layer 210 is silicon nitride (SiN), deposited using, for example, low pressure chemical vapor deposition (LPCVD). Other materials with which hard mask layer 210 may be formed include, but are not limited to, hafnium oxide ($HfO_2$) or titanium oxide. Hard mask layer 210 is of a sufficient thickness to protect portions of semiconductor substrate 120 from the addition of dopants in later steps. In one embodiment, hard mask layer 210 is between 10 nm and 50 nm thick and is preferably about 30 nm thick. A person of ordinary skill in the art would recognize that chemical-mechanical planarization (CMP) steps may be inserted before and after the deposition of hard mask layer 210 to ensure that the top surfaces of both semiconductor substrate 120 and hard mask layer 210 are relatively flat. The process of patterning hard mask layer 210 to define source and drain terminals on semiconductor substrate 120 involves the use of standard photolithographic processes to define the pattern of source and drain terminals in a layer of photoresist (not shown) deposited on hard mask layer 210. In various embodiments, standard photolithographic processes are used to remove a portion of the photoresist layer corresponding to the area of semiconductor substrate 120 which is to be doped in later steps. The source and drain terminal patterns defined in the photoresist layer are formed into hard mask layer 210 by removing hard mask layer 210 from the areas not protected by the pattern in the photoresist layer. A portion of hard mask layer 210 is removed using, for example, reactive ion etching (RIE). RIE uses chemically reactive plasma, generated by an electromagnetic field, to remove various materials. A person of ordinary skill in the art will recognize that the type of plasma used will depend on the material of which hard mask layer 210 is composed, or that other etch processes, e.g., wet chemical etch, laser ablation, etc., may be used.

Figure 3A:
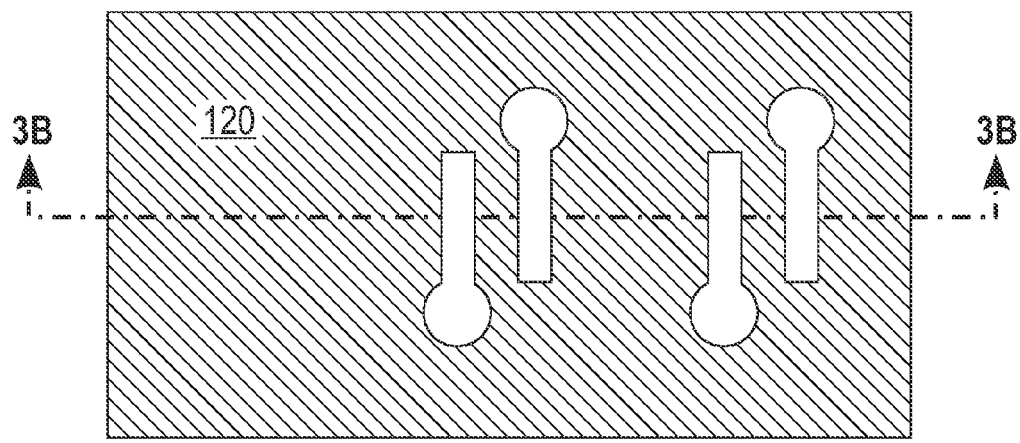
FIG. 3A depicts a top view of doped regions of the semiconductor substrate which form source and drain terminals of a MOSFET transistor, in accordance with an embodiment of the invention.
Figure 3B:
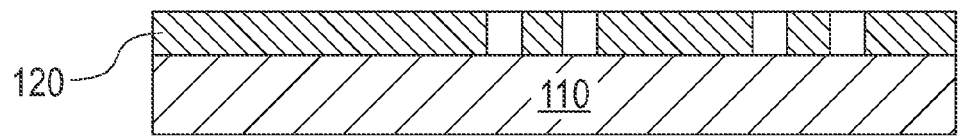
FIG. 3B depicts a section view of doped regions of the semiconductor substrate which form source and drain terminals of a MOSFET transistor, in accordance with an embodiment of the invention.

FIGS. 3A and 3B illustrate a top and section view of semiconductor substrate 120 with doped regions for the source and drain of the device and the removal of hard mask layer 210, in accordance with an embodiment of the invention. In the depicted embodiment, the portion of semiconductor substrate 120 to be doped is defined by the pattern in hard mask layer 210 and/or the layer of photoresist. In other embodiments, a layer of photoresist alone is used to define the pattern in semiconductor substrate 120 to be doped, and hard mask layer 210 is not included in such embodiments. The type of dopant is selected based on the type of MOSFET which is to be created. For example, an nFET type of transistor is doped with an n-type material such as phosphorus. Similarly, a pFET type of transistor is doped with a p-type material such as boron. In general, hard mask layer 210 is used to protect the areas of semiconductor substrate 120 which are not to be doped while the portions of semiconductor substrate 120 which are not protected by hard mask layer 210 are doped.

In various embodiments, the source and drain terminals are constructed such that the separation between a source terminal and its respective drain terminal is between 1 nm and 6 nm. In the depicted embodiment of the invention the separation between the source and drain terminals of the device is between 1 nm and 2 nm. Additionally, in some embodiments, multiple transistors may be present along nano-channel 500 for the purpose of re-reading a portion of the same strand of DNA in order to facilitate noise reduction, error correction, or any other process intended to increase the accuracy or speed of reading a sequence of DNA base pairs, by including the use of multiple transistors. These embodiments may include additional data processing components or the use of software elements not included in the depicted embodiment.

Remaining portions of hard mask layer 210 are removed once the source and drain terminals have been formed in semiconductor substrate 120 through the process of doping semiconductor substrate 210. Hard mask layer 210 is removed using, for example, RIE. RIE uses chemically reactive plasma, generated by an electromagnetic field, to remove various materials. A person of ordinary skill in the art will recognize that the type of plasma used will depend on the material of which hard mask layer 210 is composed, or that other etch processes, e.g., wet chemical etch, laser ablation, etc., may be used.

Figure 4A:
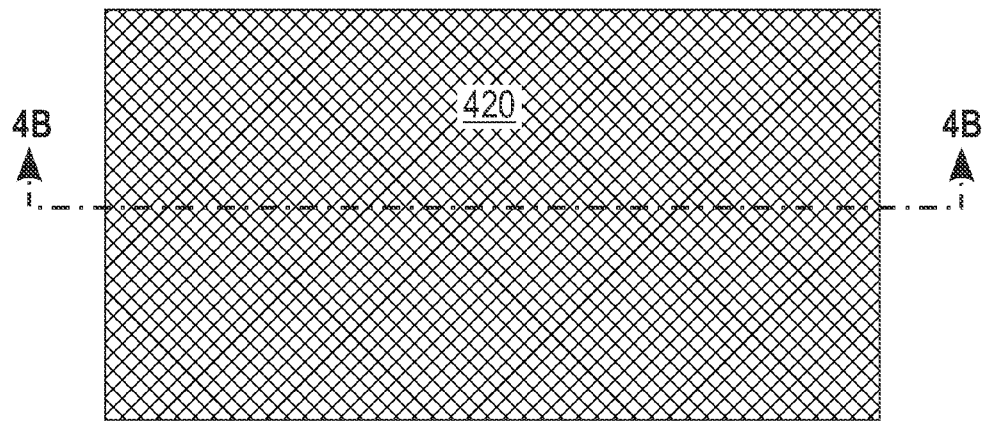
FIG. 4A depicts a top view of deposition of a dielectric layer and an insulator layer, in accordance with an embodiment of the invention.
Figure 4B:
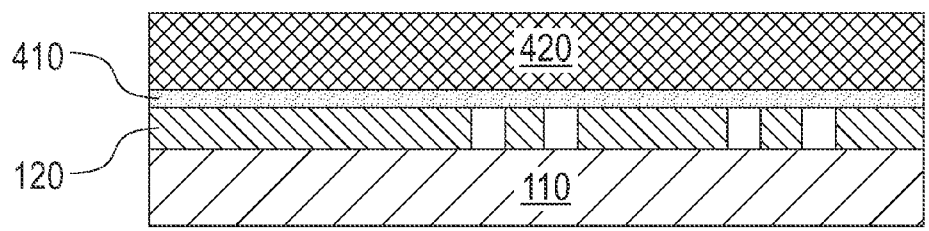
FIG. 4B depicts a section view of deposition of a dielectric layer and an insulator layer, in accordance with an embodiment of the invention.

FIGS. 4A and 4B illustrate top and section views of the deposition of dielectric layer 410 and insulator 420, in accordance with an embodiment of the invention. In a preferred embodiment, dielectric layer 410 is a high-k dielectric such as Hafnium oxide. In general, the purpose of dielectric layer 410 is to prevent electrical conduction between a strand of DNA and the source and drain terminals present in semiconductor substrate 120. Electric fields created by the charge and polarization of individual nucleotides within the strand of DNA are able to pass through dielectric layer 410, however the material of which dielectric layer 410 is composed must not be conductive in order for the device to function correctly. Insulator 420 is deposited on dielectric layer 410 and can be composed of $SiO_2$, $Si_3N_4$ or other dielectric materials. It should be appreciated by one skilled in the art that additional CMP steps may be present before and after the deposition of both dielectric layer 410 and insulator 420. In some embodiments, dielectric layer 410 is formed by oxidizing the top portion of semiconductor substrate 120 using a process such as plasma oxidation, plasma nitridation, thermal oxidation, etc.

Figure 5A:
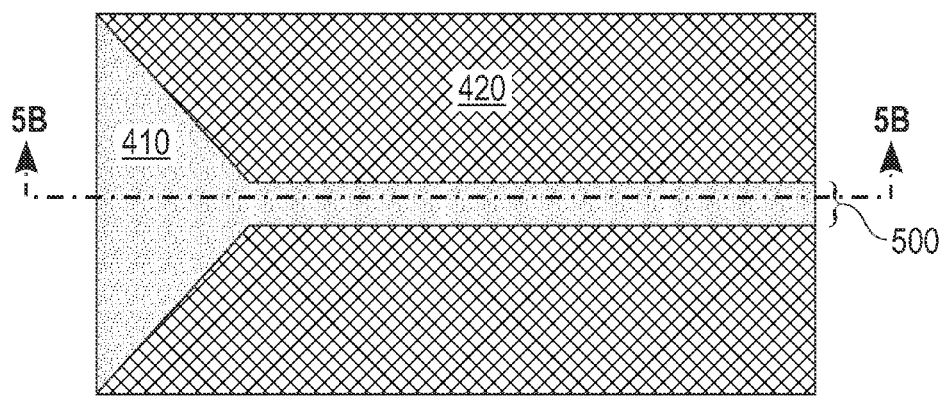
FIG. 5A depicts a top view of a nano-channel formed in the insulator layer, in accordance with an embodiment of the invention.
Figure 5B:
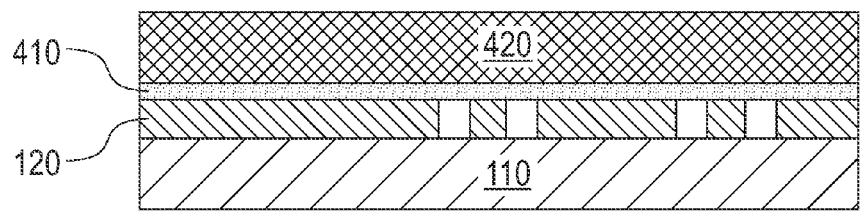
FIG. 5B depicts a section view of a nano-channel formed in the insulator layer, in accordance with an embodiment of the invention.

FIGS. 5A and 5B depict top and section views of formation of nano-channel 500, according to an embodiment of the invention. Nano-channel 500 is created by etching a portion of insulator 420 using, for example, wet chemical etching or dry etching. In one embodiment, standard photolithographic processes are used to define the pattern of nano-channel 500 in a layer of photoresist (not shown) deposited on insulator 420. The nano-channel pattern may then be formed in insulator 420 by removing insulator 420 from the areas not protected by the pattern in the photoresist layer. Insulator 420 is removed using, for example, RIE. A person of ordinary skill in the art will recognize that the type of plasma used will depend on the material of which insulator 420 is composed, or that other etch processes, e.g., wet chemical etch, laser ablation, etc., may be used. It should also be appreciated that the process used to etch the desired portion of insulator 420 must be selected such that the process does not remove any portion of dielectric layer 410, as the presence of dielectric layer 410 is required for the operation of the device. In general, nano-channel 500 is formed by removing a portion of insulator 420 in order to facilitate the movement and positioning of a strand of DNA over the source and drain terminals formed in semiconductor substrate 120. In various embodiments, nano-channel 500 has a width of between 5 nm and 100 nm, however in preferred embodiments nano-channel 500 has a width of roughly 10 nm. In the depicted embodiment, the removed portion of insulator layer 420 gradually narrows to form nano-channel 500. This narrowing portion may not be present in other embodiments of the invention, and additional elements may be added to ensure that strands of DNA are able to enter the nano-channel in such embodiments.

In general, the purpose of nano-channel 500 is to guide the movement of a strand of DNA such that the strand of DNA passes directly over the source and drain terminals formed in semiconductor substrate 120. Situations where self-avoiding polymers such as DNA are enclosed in very narrow environments (such that the width of the environment is less than the radius of gyration of the polymer), such as nano-channel 500, prevent the polymer from folding back on itself, and yield a uniform distribution of monomers (such as DNA nucleotides) throughout the length of the polymer, which provide an ideal environment for sequencing portions of DNA.

A given nucleotide or group of nucleotides present between the source and drain terminals of the device acts as the gate terminal in the current MOSFET device. A field-effect resulting from the charge or polarity of the given nucleotide or combination of nucleotides is identified based on the amount of current between the source and drain terminals of the device. The amount of current present is the result of the change in conductivity of the portion of semiconductor substrate 120 between the source and drain terminals due to the field effect generated by the nucleotide or group of nucleotides present in the active area. It should be appreciated that the number of consecutive nucleotides contributing to the overall field-effect measured by the device is determined by the separation between the source and drain terminals. In the depicted embodiment, the separation between the source and drain terminals is 6 nm. On average, the separation between consecutive nucleotides in a strand of DNA is measured to be 0.34 nm. Based on this information, a transistor with a source-drain separation of 6 nm would facilitate sequencing 18 nucleotides at a time. Similarly, in a preferred embodiment, a transistor with a source-drain separation of 1 nm would facilitate scanning only three nucleotides at a time. In general, a smaller source-drain separation is preferred because the field-effect generated by a single nucleotide is more identifiable when fewer nucleotides are present in the active area.

Before a strand of DNA can be read, a voltage source is used to apply a voltage between the source and drain terminals of the device. In various embodiments the voltage applied between the source and drain terminals of the device depends on the separation between the source and drain terminals. In general, the voltage source is capable of applying a constant voltage and measuring any current flow between the source and drain terminals of the device which result from a field effect generated by a nucleotide or group of nucleotides currently present in the active area. In some embodiments, the voltage source is a device connected to a computer or another electronic device capable of storing and analyzing information related to the change in the current flow between the source and drain terminals over time. The process of sequencing DNA involves recording the change in current flowing between the source terminal and the drain terminal of the device in order to determine the field-effect generated by the charge and polarity of the portion of nucleotides currently being sequenced. As a strand of DNA moves through the nano-channel, nucleotides continuously pass through the active area between the source and drain terminals where the field effect is measured. In some embodiments, before the sequencing of an unknown portion of DNA begins, the device is calibrated by using a strand of DNA containing a known sequence of nucleotides to determine the expected field-effects for various combinations of nucleotides. In these embodiments, data collected during calibration is recorded in a table listing the expected field-effect for each possible combination of nucleotides. For example, in an embodiment where four nucleotides are read at a time, there are 256 ($4^4$) possible combinations of nucleotides which can be present in the active area at any given time. Identifying the specific combination of nucleotides currently present and contributing to the field-effect is performed by measuring the current present between the source and drain terminals and comparing this value to the current expected for various known combinations of nucleotides.

In embodiments where the separation between the source and drain terminals is larger, more nucleotides may be able to fit between the source and drain terminals. The increase in the number of nucleotides which can fit between the source and drain terminals can cause an exponential increase in the number of possible combinations of nucleotide sequences which much be chosen from in order to determine the current sequence of nucleotides present between the source and drain terminals.

One such example would be the case of a 10 nm separation between the source and drain terminals, which can allow roughly 30 nucleotides to be present in the active area. With 30 nucleotides present in the active area, and four possible bases that each nucleotide can contain (adenine (A), thymine (T), guanine (G), cytosine (C)), the total number of possible combinations ($4^{30}$) is extremely large. In these embodiments it is much more desirable to examine only the changes in the current between the source and the drain to determine which specific nucleotides are entering and leaving the active area to cause the change in the field-effect. For example, in an embodiment where the active area is sufficiently wide to accommodate 4 nucleotides, the current set of nucleotides present in the active area is determined to be GTAC. As the strand of DNA moves across the active area, the set of nucleotides changes to CTAC, and from this information it can be determined that the G nucleotide present in the initial set of nucleotides has left the active area and been replaced by a C nucleotide. As the strand of DNA continues to pass along the active area, the order in which new nucleotides arrive to the active area can be used to determine the order in which nucleotides are present along the strand of DNA. This information can be verified by observing the order in which the same nucleotides leave the active area, or arrive at a second active area present along nano-channel 500.

In the depicted embodiment, insulator 420 is etched to form nano-channel 500 which is used to position a portion of DNA directly above the source and drain terminals (see FIG. 3). In some embodiments, a nano-tunnel may be formed by adding a planar portion of insulating material above the nano-channel to form a portion of material present above nano-channel 500. In other embodiments, a nano-tunnel is formed by horizontally etching a portion of insulator 420 and preserving the topmost portion of insulator 420 to form a nano-tunnel with a portion of insulator 420 present above the nano-tunnel.

Figure 6A:
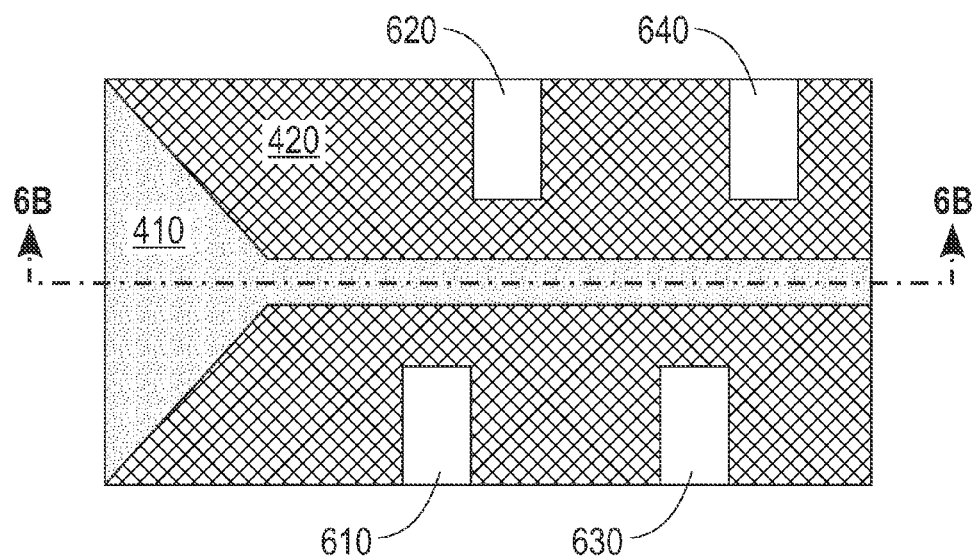
FIG. 6A depicts a top view of formation of contacts for the source and drain terminals of the current MOSFET transistor, in accordance with an embodiment of the invention.
Figure 6B:
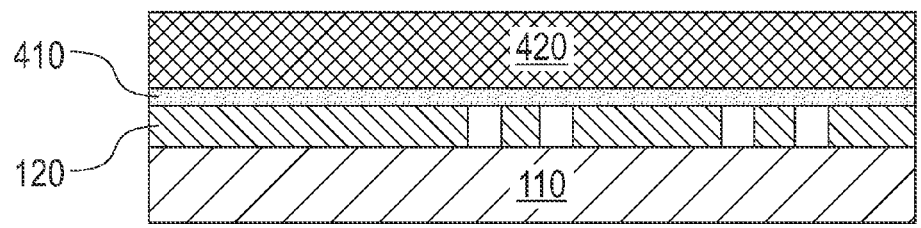
FIG. 6B depicts a section view of formation of contacts for the source and drain terminals of the current MOSFET transistor, in accordance with an embodiment of the invention.

FIGS. 6A and 6B depict top and section views of formation of metal contacts 610, 620, 630, and 640. Metal contacts 610, 620, 630, and 640 are used for connecting the current MOSFET device to other electrical components such as a computer or other device for processing and interpreting the signal transmitted from the current MOSFET device. A person of ordinary skill in the art will recognize that the formation of contacts 610, 620, 630, and 640 includes the steps of etching a portion of insulator 420, dielectric layer 410, and semiconductor substrate 120 and depositing a contact material into the etched portion of the layer. A contact material can comprise a metal such as tungsten, titanium, titanium nitride, or copper, and may be deposited by a process such as chemical vapor deposition (CVD). After the contact metal used to form contacts 610, 620, 630, and 640 is deposited, CMP may be used to remove excess contact material present above the top of insulator 420.

It should be appreciated that although the depicted embodiment illustrates the formation of four metal contacts, other embodiments may include the formation of two, four, six, eight, or any even number of metal contacts. In general, two metal contacts are formed for each transistor present along nano-channel 500. In the depicted embodiment, the two transistors present along nano-channel 500 require the formation of four metal contacts. In the depicted embodiment, contacts 610 and 630 connect the source terminals of the first and second transistors present along nano-channel 500 to outside electrical components respectively. Similarly, contacts 620 and 640 connect the drain terminals of the first and second transistors present along nano-channel 500 to outside electrical components respectively.

The method as described above is used in the fabrication of integrated circuit chips.

The resulting semiconductor device may be included on a semiconductor substrate consisting of many devices and one or more wiring levels to form an integrated circuit chip. The resulting integrated circuit chip(s) can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Having described preferred embodiments of a MOSFET device for sequencing DNA (which are intended to be illustrative and not limiting), it is noted that modifications and variations may be made by persons skilled in the art in light of the above teachings. It is therefore to be understood that changes may be made in the particular embodiments disclosed which are within the scope of the invention as outlined by the appended claims.

What is claimed is:

1. A method, the method comprising:
   providing a sensor comprising:
      a buried oxide layer;
      a substrate layer formed on and above the buried oxide layer;
      a first source region formed in a first portion of the substrate layer and a first drain region formed in a second portion of the substrate layer, the first source region and the first drain region spaced a first distance apart;
      a dielectric layer formed on the substrate layer;
      an insulative layer formed on the dielectric layer;
      a nano-channel formed in the insulative layer, wherein the nano-channel passes over the first source region and the first drain region such that each of the first source region and the first drain region are only below a bottom side of the nano-channel; and
      a contact for each source and drain region;
   connecting a voltage source across the first source region and the first drain region, the voltage source capable of measuring current flow through the first source region and the first drain region when at least one DNA nucleotide is present in the nano-channel between the first source region and the first drain region;
   providing a strand of DNA in the nano-channel, wherein a first portion of the strand of DNA is present in the nano-channel between the first source region and the first drain region; and
   measuring, by one or more processors, a first current flow between the first source region and the first drain region.

2. The method of claim 1, further comprising:
   measuring, by one or more processors, a second current flow between the first source region and the first drain region when a second portion of the strand of DNA is present in the nano-channel between the first source region and the first drain region.

3. The method of claim 2, further comprising:
   determining, by one or more processors, a first set of one or more DNA nucleotides corresponding to the first current flow;

determining, by one or more processors, a second set of one or more DNA nucleotides corresponding to the second current flow; and identifying, by one or more processors, at least one different DNA nucleotide present within the first set of one or more DNA nucleotides and the second set of one or more DNA nucleotides.

4. The method of claim 2, further comprising:

calculating, by one or more processors, a difference between the measured first current flow and the measured second current flow; and identifying, by one or more processors, a change in presence of one or more DNA nucleotides between the first portion of the strand of DNA and the second portion of the strand of DNA based, at least in part, on the calculated difference.

5. The method of claim 1, wherein the sensor further comprises:

a second source region and a second drain region formed in the substrate layer, the second source region and the second drain region spaced a second distance apart.

6. The method of claim 5, further comprising:

connecting a voltage source across the second source region and the second drain region, the voltage source capable of measuring current flow through the second source region and the second drain region when at least one DNA nucleotide is present in the nano-channel between the second source region and the second drain region;

measuring, by one or more processors, a third current flow between the second source region and the second drain region, wherein the first portion of the strand of DNA is present in the nano-channel between the second source region and the second drain region;

comparing, by one or more processors, the measured first current flow and the measured third current flow; and verifying, by one or more processors, whether the measured first current flow and the measured third current flow are equal to within a predetermined threshold.

7. The method of claim 5, wherein the first distance and the second distance are equal.

8. The method of claim 5, wherein the first distance is of a different length than the second distance.

9. The method of claim 1, wherein the first distance is less than or equal to 6 nanometers.

* * * * *